(12) United States Patent
Attolini

(10) Patent No.: US 6,318,360 B1
(45) Date of Patent: Nov. 20, 2001

(54) SINGLE-UNIT APPARATUS FOR AEROSOL THERAPY WITH INTEGRATED COMPRESSOR GROUP AND ASSOCIATED METHOD OF ASSEMBLY

(75) Inventor: Lorenzo Attolini, Parma (IT)

(73) Assignee: Medel S.p.A., Torille (IT)

( * ) Notice: Subject to any disclaimer, the term of this patent is extended or adjusted under 35 U.S.C. 154(b) by 0 days.

(21) Appl. No.: 09/384,374

(22) Filed: Aug. 27, 1999

(30) Foreign Application Priority Data

Sep. 10, 1998 (IT) .............................. PR98A0055

(51) Int. Cl.$^7$ .................................. A61M 11/00
(52) U.S. Cl. ............... 128/200.14; 128/200.22; 128/203.12; 128/204.24
(58) Field of Search .................. 128/200.14, 200.22, 128/200.19, 204.18, 201.11, 205.18, 203.12, 204.24

(56) References Cited

U.S. PATENT DOCUMENTS

| | | | |
|---|---|---|---|
| 4,080,103 | * 3/1978 | Bird | 417/3 |
| 4,826,510 | * 5/1989 | McCombs | 55/179 |
| 4,949,715 | * 8/1990 | Brugger | 128/204.21 |
| 5,297,545 | * 3/1994 | Infante | 128/204.18 |
| 5,398,676 | * 3/1995 | Press et al. | 128/204.23 |
| 5,570,682 | * 11/1996 | Johnson | 128/200.14 |
| 5,603,314 | * 2/1997 | Bono | 128/200.21 |

* cited by examiner

Primary Examiner—John G. Weiss
Assistant Examiner—V. Srivastava
(74) Attorney, Agent, or Firm—Pillsbury Winthrop LLP

(57) ABSTRACT

Apparatus for aerosol therapy which is designed to draw air from the environment and transmit it to the user, comprising an optional external casing housing a motor, an optional fan for cooling and a compressor group which has a terminal block interfaced with the exterior by means of an intake duct and by means of a delivery duct, wherein the terminal block incorporates the intake duct and the delivery duct and interfaces directly with the exterior by means of an intake socket and a delivery socket designed to fit the profile of the external casing.

10 Claims, 3 Drawing Sheets

Figure 1:
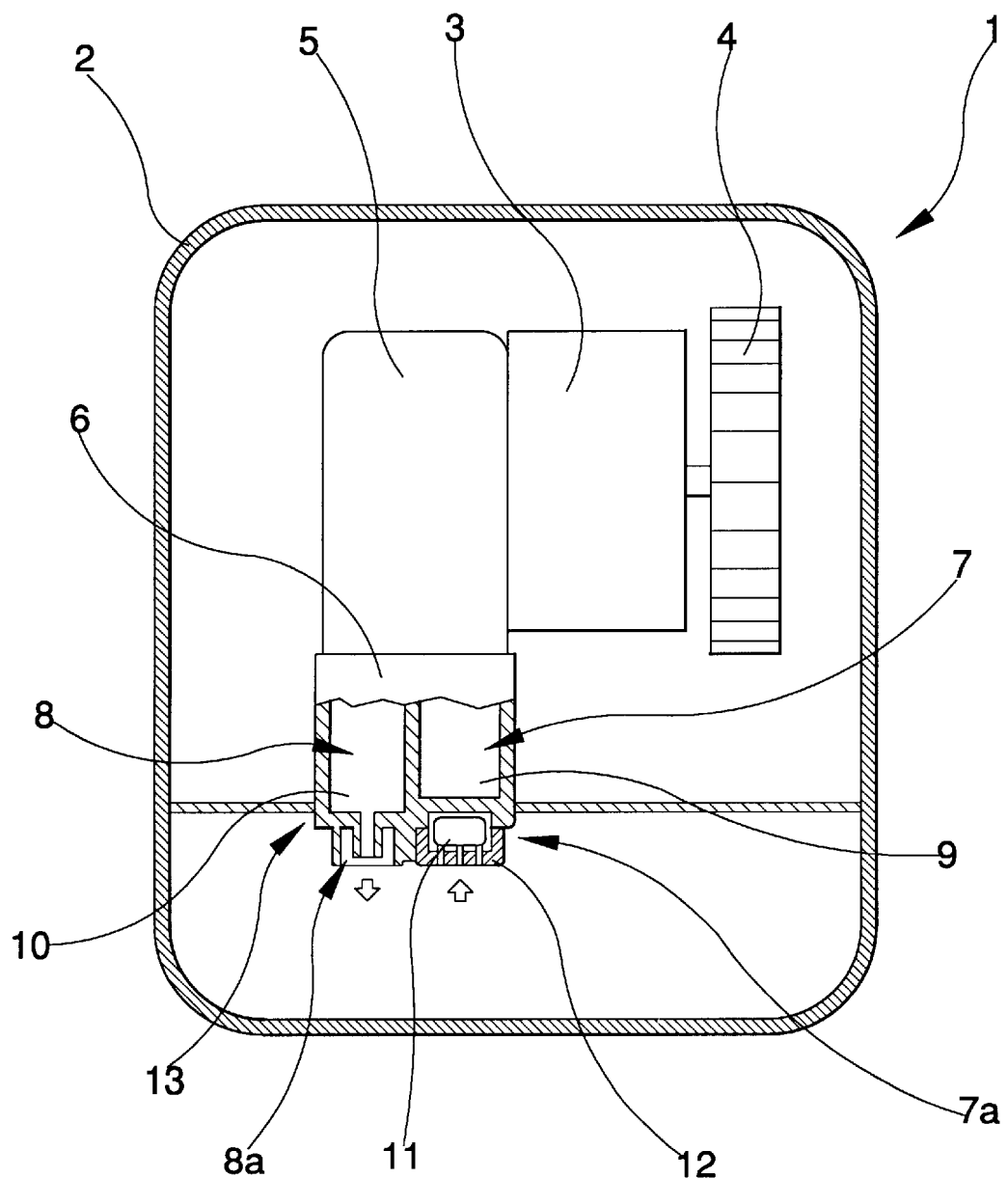
Figure 2:
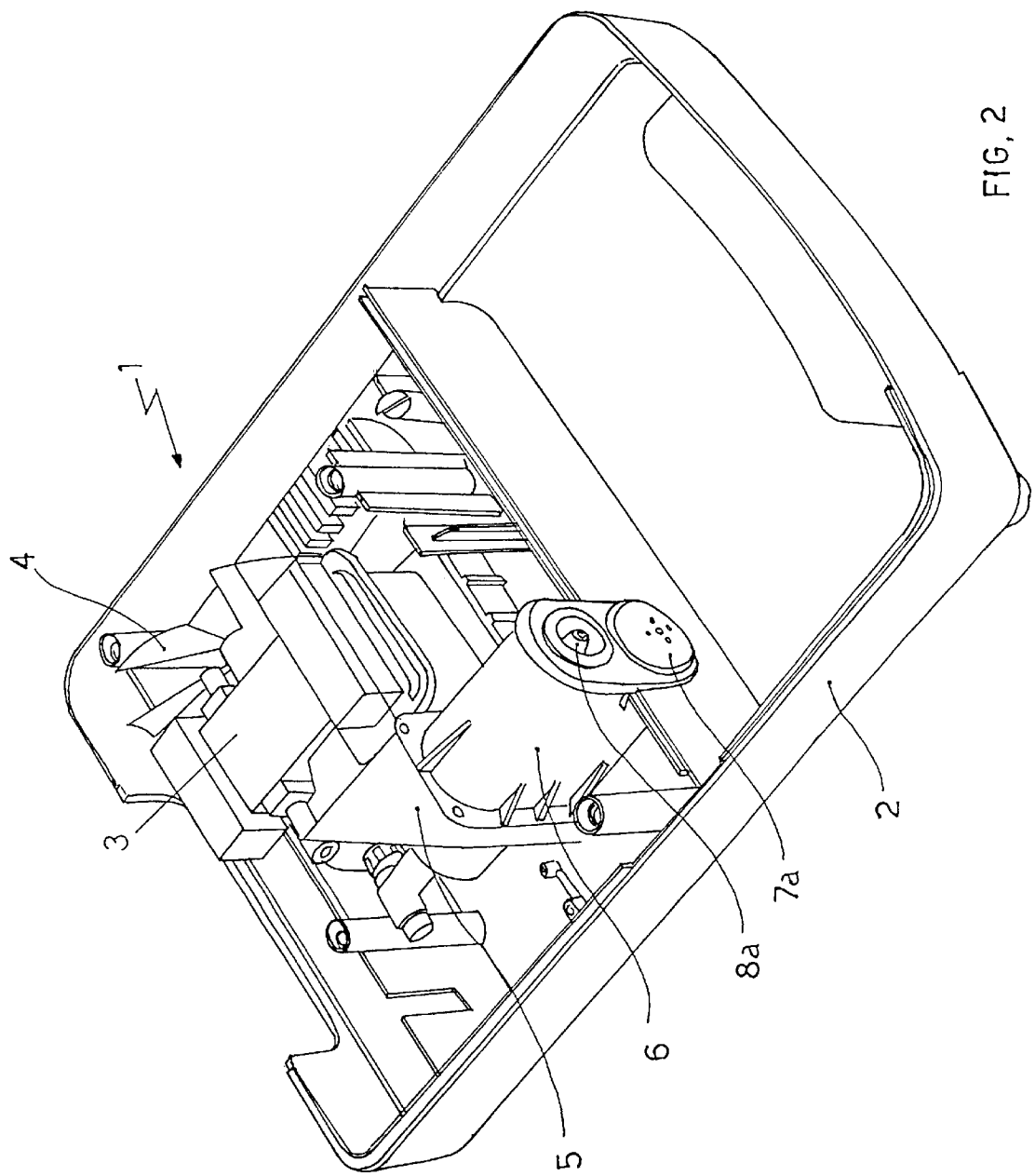
Figure 3:
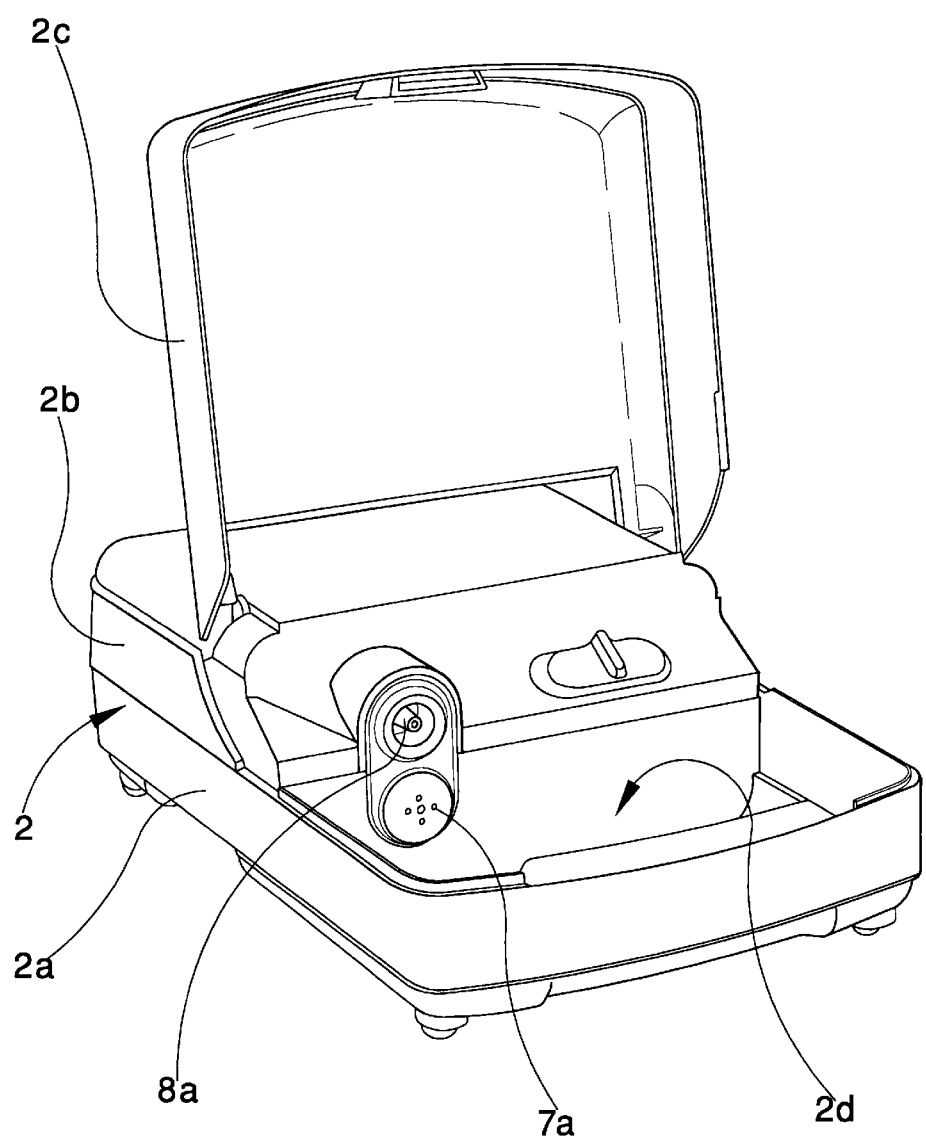

SINGLE-UNIT APPARATUS FOR AEROSOL THERAPY WITH INTEGRATED COMPRESSOR GROUP AND ASSOCIATED METHOD OF ASSEMBLY

BACKGROUND OF THE INVENTION

The present invention relates to a single-unit apparatus for aerosol therapy with an integrated compressor group and to an associated method of assembly.

In the sector of aerosol therapy, apparatus consisting of an external casing generally made of plastic and designed to house a compressor/motor group which draws air from the outside and delivers it to the atomizing container for therapeutic treatment are used.

The compressor draws air from the outside by means of an intake duct and outputs air for the treatment by means of a delivery duct. Compressors are known where the intake duct consists, in the direction of the components encountered by the air flow, of an external filter located on the casing, an intake pipe, an intake silencer and finally another pipe for connection to the compressor; the delivery duct consists of a safety collar, a delivery silencer, a connection pipe and finally another safety collar before interfacing with the user by means of the external casing.

The structure for connection with the exterior is therefore complex and costly, both in terms of the material used and in terms of assembly time. In fact, after the compressor/motor group has been fixed by means of screws or by means of mounting on rubber supports, each connection pipe must be positioned and secured by means of clamps or other securing means.

In particular, it is necessary to assemble (ie. engage and clamp) the intake pipe and the connection pipe onto the intake duct, while the two connection pipes must be engaged and clamped onto the delivery duct.

Moreover, an apparatus constructed in this manner, is able to function only if the compressor is incorporated in a casing which interfaces it with the external environment, creating a stable support for the intake inlet and outlet of the delivery air.

SUMMARY OF THE INVENTION

The object of the present invention is that of eliminating the abovementioned drawbacks and providing a single-unit apparatus for aerosol therapy with an integrated compressor group and an associated method of assembly which elminates the intake and delivery connection pipes and which allows direct interfacing of the compressor with the external environment.

Said objects are fully achieved by the single-unit apparatus for aerosol therapy with integrated compressor group and an associated method of assembly according to the present invention, as described by the contents of the claims indicated below.

In particular, the compressor group comprises a terminal block which is interfaced with the exterior by means of an intake duct and by means of a delivery duct and which is structured so as to incorporate the intake duct and the delivery duct themselves and interface directly with the exterior by means of a socket for the intake and a socket for the delivery which are designed to fit the profile of the external casing.

In greater detail, the terminal block of the compressor group comprises two separate chambers which are designed to form, respectively, the intake duct and the delivery duct having the functions of a connection and silencer, thus avoiding pipes, securing clamps and external silencers.

Moreover, according to the method of assembly, comprising the steps of assembly of the terminal block on the compressor group and positioning of the motor and the compressor group in the external casing, positioning is performed by means of simple engagement so that the intake sockets and the delivery socket fit the profile of the external casing and are immediately accessible for the user.

BRIEF DESCRIPTION OF THE DRAWINGS

These and other characteristic features will emerge more clearly from the following description of a preferred embodiment illustrated, purely by way of a non-limiting example, in the accompanying plates of drawings, in which:

FIG. 1 shows a plan view of the apparatus without cover and partially sectioned;

FIG. 2 shows a perspective view of the apparatus without cover;

FIG. 3 shows a perspective view of the apparatus in the configuration ready for use.

DESCRIPTION OF THE PREFERRED EMBODIMENTS

With reference to the figures, 1 denotes an apparatus for aerosol therapy enclosed in an external casing 2 made of plastic material and comprising a bottom part 2*a* and a top part 2*b* provided with cover 2*c* for closing a compartment 2*d* intended to contain accessories of the apparatus itself.

The external casing 2 houses internally a motor 3 and a fan 4 of a known type for cooling, which may be optionally replaced with another cooling device, in addition to a compressor group 5.

The compressor group 5, comprising an original terminal block 6, draws in air from the outside by means of a intake duct 7 and delivers air to an atomizing container for the aerosol therapy treatment (not shown and of the known type) by means of a delivery duct 8 which emerges into a socket 8*a* into which a flexible pipe connecting the socket to the atomizing container is normally fixed by the user. The two ducts are selected by means of a valve of a substantially known type not shown in the Figures. The intake duct 7 is connected to the exterior by means of an intake socket 7*a* comprising a filter 11 and an associated protective closing cover for allowing the periodic replacement of the filter 11; the delivery duct 8 is connected to the exterior by means of the delivery socket 8*a* which is designed to be connected to the atomizing container used for the therapeutic treatment.

The terminal block 6 is formed in an original manner so as to incorporate in it both the intake duct 7 and the delivery duct 8.

The terminal block 6 in fact consists of two chambers 9 and 10 which are separate but formed in the same block of material forming the terminal block 6 and having respectively, the function of an intake duct 7 and a delivery duct 8.

As a result of the abovementioned chambers, it is possible to eliminate the connection pipes and the respective fixing clamps. Moreover, since the intake and delivery silencers generally consist of a simple air volume, the chambers 9 and 10 are also able to perform the function of silencers, thus avoiding the presence of a further external element.

The intake socket 7*a* and the delivery socket 8*a* are formed directly on the terminal block 6 and connect the the chambers 9 and 10 to the exterior; in the case of the intake duct, the filter 11 and the associated cover 12 are also assembled directly on the terminal block 6, whereas, in the case of the delivery duct, the socket 8a allows the direct connection to the atomizing container, if necessary, via a flexible pipe.

The original configuration of the terminal block 6, with the presence of the intake socket 7a and the delivery socket 8a, allows the compressor group 5 to interface directly with the exterior without passing via the external casing 2; in this way the apparatus for aerosol therapy could also function independently of the external casing, ie. being connected directly to the container.

The external casing 2 is structured in a substantially known manner; however, it does not have a user interface zone for the intake socket 7a and the delivery socket 8a, but simply comprises a seat 13 for the abovementioned sockets formed on the terminal block 6.

Owing to the original configuration of the terminal block 6, the method of assembly of the apparatus 1 is also simplified and shortened. In fact, after the terminal block 6 has been assembled on the compressor group 5, it is sufficient to house the compressor group 5 inside the external casing 2 without the need for connection pipes, clamps and silencers.

The assembly steps envisage firstly assembly of the terminal block 6 on the compressor group 5.

Then the compressor/motor group is housed on the overturned upper half of the casing 2 so that the sockets 7a and 8a for the intake and delivery are positioned inside the seat 13 formed in the casing 2.

Finally, the bottom half of the casing 2 is positioned and fixed and then the assembly turned over so as to obtain the complete apparatus 1.

Fixing of the compressor/motor group inside the external casing 2 is performed by means of simple pressure engagement and is ensured by rubber supports which are located both on the bottom part and on the top part of the casing.

It is obvious that this procedure reduces the number of parts outside the compressor group necessary for correct operation of the apparatus and simplifies and shortens considerably the method of assembly, consequently reducing the costs both in terms of material and labor costs.

What is claimed is:

1. An apparatus for aerosol therapy which is designed to draw air from the exterior environment and transmit it to the a user, comprising:
    a motor and
    a compressor group which has a terminal block interfacing with the exterior environment by means of an intake duct and by means of a deliver duct, wherein the terminal block incorporates the intake duct and the delivery duct and interfaces directly with the exterior environment by means of an intake socket and a delivery socket located on an end part of the respective intake and delivery ducts,
    wherein the terminal block of the compressor group comprises:
        a chamber arranged to form a portion of the intake duct is also arranged to form a connection and silencer; and
        a chamber arranged to form a portion of the delivery duct is also arranged to form a connection and silencer;
        said chambers being separate from each other, but being formed from a same block of material from which the terminal block is made.

2. The apparatus for aerosol therapy as claimed in claim 1, and further including an external casing for housing the motor and compressor group, wherein the intake and delivery sockets are formed so as to fit a profile of the external casing.

3. The apparatus for aerosol therapy as claimed in claim 1, and further including an external casing for housing the motor and compressor group, wherein the chamber acting as the intake duct comprises the intake socket which is directly formed on the terminal block and is formed to fit a profile of the external casing.

4. The apparatus for aerosol therapy as claimed in claim 3, wherein the intake socket comprises a filter and an associated cover which are assembled directly on the terminal block.

5. The apparatus for aerosol therapy as claimed in claim 1, and further including an external casing for housing the motor and compressor group, wherein the chamber acting as the delivery duct comprises the delivery socket which is directly formed on the terminal block and is formed to fit a profile of the external casing.

6. The apparatus for aerosol therapy as claimed in claim 1, and further including an external casing for housing the motor and compressor group, wherein the external casing comprises a seat which is designed to receive the intake socket and the delivery socket formed on the terminal block of the compressor group.

7. The apparatus for aerosol therapy as claimed in claim 1 and further comprising a fan for cooling the apparatus.

8. The apparatus for aerosol therapy as claimed in claim 4 and further comprising a fan for cooling the apparatus.

9. The apparatus for aerosol therapy as claimed in claim 5 and further comprising a fan for cooling the apparatus.

10. A method of assembly for an apparatus for aerosol therapy comprising the steps of:
    assembling a terminal block on a compressor group, and
    positioning a motor, the compressor group and the terminal block in an external casing, wherein positioning of the compressor group is performed by means of simple engagement so that the intake socket and the delivery socket are immediately accessible for a user.

* * * * *